US009480851B2

(12) United States Patent
Kroll

(10) Patent No.: US 9,480,851 B2
(45) Date of Patent: Nov. 1, 2016

(54) MULTI-MODAL ELECTROTHERAPY METHOD AND APPARATUS

(71) Applicant: Galvani, Ltd., Edina, MN (US)

(72) Inventor: Mark W. Kroll, Crystal Bay, MN (US)

(73) Assignee: Galvani, Ltd., Edina, MN (US)

( * ) Notice: Subject to any disclaimer, the term of this patent is extended or adjusted under 35 U.S.C. 154(b) by 0 days.

(21) Appl. No.: 14/248,815

(22) Filed: Apr. 9, 2014

(65) Prior Publication Data
US 2014/0303679 A1 Oct. 9, 2014

Related U.S. Application Data

(62) Division of application No. 13/567,699, filed on Aug. 6, 2012, now Pat. No. 8,718,759.

(60) Provisional application No. 61/574,524, filed on Aug. 4, 2011.

(51) Int. Cl.
*A61N 1/362* (2006.01)
*A61N 1/39* (2006.01)
*A61N 1/378* (2006.01)

(52) U.S. Cl.
CPC .......... *A61N 1/3975* (2013.01); *A61N 1/3621* (2013.01); *A61N 1/3627* (2013.01); *A61N 1/3782* (2013.01); *A61N 1/3962* (2013.01); *A61N 1/3981* (2013.01)

(58) Field of Classification Search
CPC ............. A61N 1/3621; A61N 1/3627; A61N 1/3782; A61N 1/3962; A61N 1/3981; A61N 1/3975
See application file for complete search history.

(56) References Cited

U.S. PATENT DOCUMENTS

| 4,407,288 | A | 10/1983 | Langer et al. |
| 4,986,270 | A | 1/1991 | Cohen |
| 5,251,624 | A | 10/1993 | Bocek et al. |
| 5,314,319 | A | 5/1994 | Nilsson et al. |
| 5,314,448 | A | 5/1994 | Kroll et al. |
| 5,391,186 | A | 2/1995 | Kroll et al. |
| 5,470,341 | A | 11/1995 | Kuehn et al. |
| 5,607,454 | A | 3/1997 | Cameron et al. |

(Continued)

FOREIGN PATENT DOCUMENTS

| EP | 0540266 | 5/1993 |
| WO | WO 2014/160930 | 10/2014 |

OTHER PUBLICATIONS

US 5,584,866, 12/1994, Kroll et al. (withdrawn).

(Continued)

*Primary Examiner* — Joseph Dietrich
(74) *Attorney, Agent, or Firm* — Patterson Thuente Pedersen, P.A.

(57) ABSTRACT

A multi-modal electrotherapy apparatus including circuitry for administering defibrillation therapy and for administering medium voltage therapy (MVT). A combined-use capacitor bank of at least one capacitor stores energy to be administered as defibrillation therapy and MVT. Combined-use discharge circuitry electrically is coupled between the combined-use capacitor bank and patient terminals for selectively administering energy from the capacitor bank according to a plurality of controllable waveforms as either defibrillation therapy or MVT. A controller is configured to cause the discharge circuitry to apply the MVT from the capacitor bank while the capacitor bank undergoes charging in preparation for administration of the defibrillation therapy.

13 Claims, 18 Drawing Sheets

(56) References Cited

U.S. PATENT DOCUMENTS

| | | |
|---|---|---|
| 5,700,281 A | 12/1997 | Brewer et al. |
| 5,735,876 A | 4/1998 | Kroll et al. |
| 5,782,883 A | 7/1998 | Kroll et al. |
| 5,871,510 A | 2/1999 | Kroll et al. |
| 6,314,319 B1 | 11/2001 | Kroll et al. |
| 6,577,102 B1 | 6/2003 | Vaisnys et al. |
| 6,760,621 B2 | 7/2004 | Walcott et al. |
| 7,383,085 B2 | 6/2008 | Olson |
| 8,483,822 B1 | 7/2013 | Gilman et al. |
| 8,718,759 B2 | 5/2014 | Kroll |
| 8,750,990 B1 | 6/2014 | Gilman et al. |
| 8,805,495 B2 | 8/2014 | Gilman et al. |
| 8,868,178 B2 | 10/2014 | Gilman et al. |
| 2002/0161407 A1* | 10/2002 | Walcott ............... A61N 1/3962 607/5 |
| 2006/0142809 A1 | 6/2006 | Kroll et al. |
| 2007/0299473 A1 | 12/2007 | Matos |
| 2014/0236248 A1 | 8/2014 | Gilman et al. |

OTHER PUBLICATIONS

European Search Report for European Application No. 12820255 mailed May 3, 2015.

International Search Report and Written Opinion for International Application No. PCT/US2012/049765 dated Dec. 3, 2012.

International Preliminary Report and Written Opinion for International Application No. PCT/US2012/049765 dated Feb. 13, 2014.

Application and File History for U.S. Appl. No. 13/567,699, filed Aug. 6, 2012, inventor Kroll.

* cited by examiner

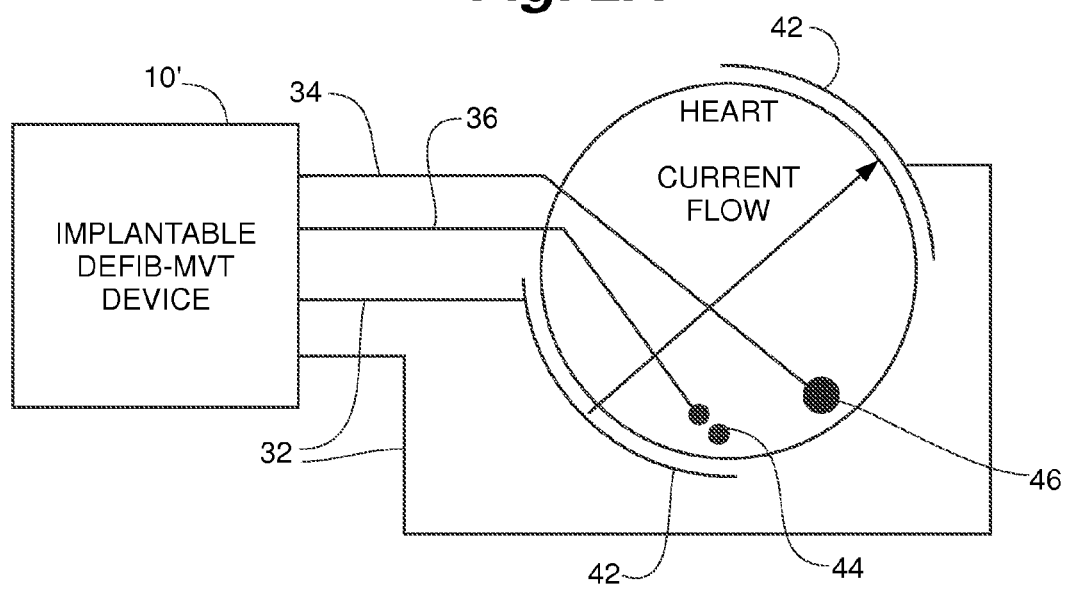

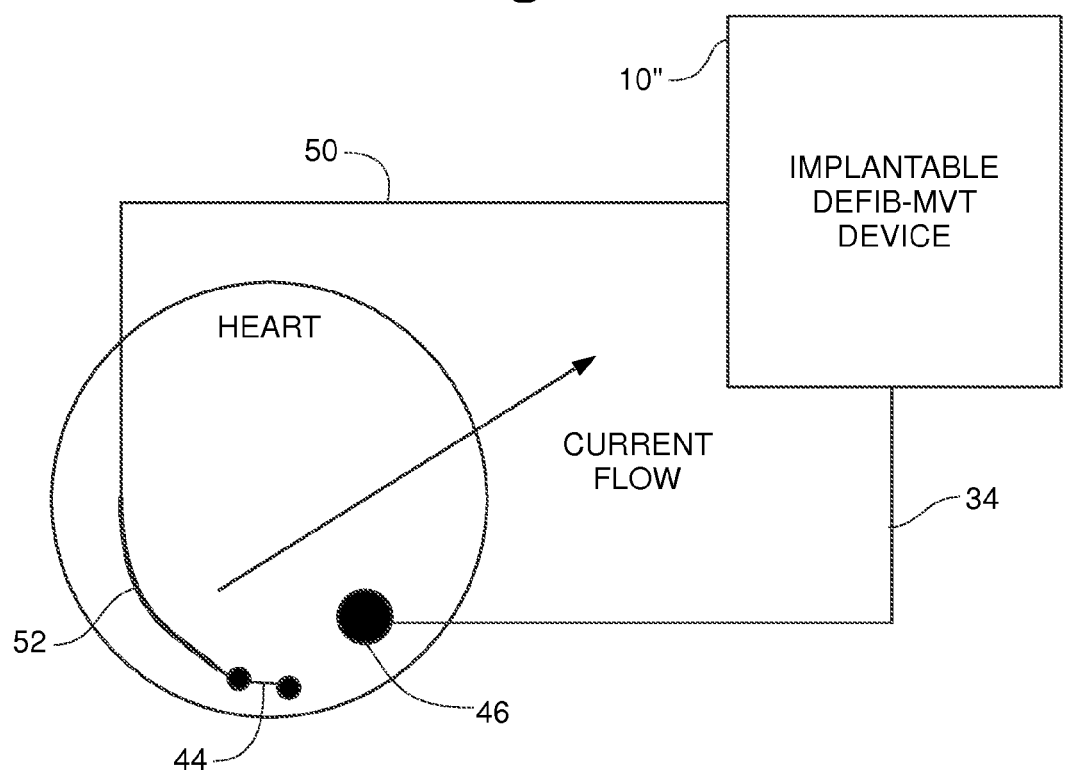

MVT ON

MVT WAVEFORM

MVT WAVEFORM

MULTI-MODAL ELECTROTHERAPY METHOD AND APPARATUS

PRIOR APPLICATIONS

This Application is a divisional application of U.S. patent application Ser. No. 13/567,699 filed Aug. 6, 2012, now U.S. Pat. No. 8,718,759, which claims the benefit of U.S. Provisional Application No. 61/574,524, filed Aug. 4, 2011, entitled "Defibrillator with Electrical CPR," which is incorporated by reference herein in its entirety.

FIELD OF THE INVENTION

The invention relates generally to treatments for individuals experiencing cardiac arrest and, more particularly, to implantable or external treatment apparatus and associated methods of operation thereof, incorporating medium voltage therapy (MVT) with defibrillation therapy.

BACKGROUND OF THE INVENTION

Cardiac arrest is a significant public health problem cutting across age, race, and gender. Defibrillators have had a major impact on dealing with cardiac arrest in that they are the only reliable treatment for VF (ventricular fibrillation).

A positive impact on cardiac arrest survival has been demonstrated with the substantial reduction in time to defibrillation provided by the widespread deployment of automated external defibrillators (AEDs) and the use of implantable cardioverter defibrillators (ICDs). Examples of AEDs are described in U.S. Pat. Nos. 5,607,454, 5,700,281 and 6,577,102 while examples of ICDs are described in U.S. Pat. Nos. 5,391,186, 7,383,085, and 4,407,288.

Research has been clear in demonstrating that the timing of resuscitation is of critical importance. For example, the probability of recovery goes down the about 5% per minute after the onset of ventricular fibrillation (VF) from a non-electrocution cardiac arrest. This knowledge led to the recent widespread deployment of AEDs, primarily in public areas with a high population concentration such as airports and shopping malls. A positive impact on cardiac arrest survival has been demonstrated due to the substantial reduction in time to defibrillation as a result of more available access to AEDs. In addition, for those patients identified as being at particularly high risk, an implantable cardioverter-defibrillator is often implanted in order to address episodes of cardiac arrest without the involvement of a rescuer.

One major challenge in the use of widely-deployed defibrillators is that defibrillation of a heart that has been in VF for a while can actually harm the heart. When the heart has been in VF for a long time, the delivery of the shock can actually lead to more dangerous rhythms such as asystole or EMD (Electro Mechanical Disassociation, a.k.a. Pulseless Electrical Activity or PEA). These problems occur after cardiac arrest because without continuing blood flow the oxygen and energy supplied to the heart tissue, is no longer sufficient to enable it to contract with the necessary force to move blood in the case of PEA; and in the case of asystole can no longer even conduct an electrical signal. Shocking a heart in this condition is unlikely to result in a pulsatile rhythm.

In the case of VF, performing CPR-type chest compressions before defibrillation and minimizing the time to defibrillation shock following the cessation of the CPR chest compressions is important in facilitating effective recovery especially in cases of long duration VF. The primary purpose of administering cardio-pulmonary resuscitation (CPR) to a cardiac arrest victim is to cause blood to circulate into the heart before shocking it. This provides two benefits: first, the distended right ventricle is compressed back to its more nearly normal size, facilitating defibrillation; second, the heart tissue is oxygenated in order to work effectively. Despite the importance of CPR-type chest compressions, they are often not performed in the field for a variety of reasons.

One approach that has been proposed for automating a treatment that can provide an effect similar to performing chest compressions is with the application of cardiac electrotherapy stimuli having an amplitude that is greater than that of pacing-type stimuli, but less than the amplitude and energy level associated with defibrillation-type stimuli. These are known in the art as medium voltage therapy (MVT). For example, U.S. Pat. No. 5,314,448 describes delivering low-energy pre-treatment pulses followed by high-energy defibrillation pulses, utilizing a common set of electrodes for both types of stimuli. According to one therapeutic mechanism of this pre-treatment, the MVT pulses cause chest constrictions similar to those of manual chest compressions of traditional CPR. The constrictions provide fresh oxygenated blood to the heart and facilitate a greater probability of successful defibrillation with a follow-on defibrillation pulse. U.S. Pat. No. 6,760,621 describes the use of MVT as pretreatment to defibrillation that is directed to reducing the likelihood of pulseless electrical activity and electromechanical dissociation conditions as a result of the defibrillation treatment. The mechanisms by which these results are achieved by MVT include a form of sympathetic stimulation of the heart. These approaches are directed to influencing the electrochemical dynamics or responsiveness of the heart tissues.

MVT has also been recognized as a way of forcing some amount of cardiac output by electrically stimulating the heart directly with stimuli that cause some heart and some skeletal muscle to contract in a controlled manner. See U.S. Pat. Nos. 5,735,876, 5,782,883 and 5,871,510. These patents describe implantable devices having combined defibrillation, and MVT capability for forcing cardiac output. U.S. Pat. No. 6,314,319 describes internal and external systems and associated methods of utilizing MVT to achieve a hemodynamic effect in the heart as part of an implantable cardioverter defibrillator (ICD) for purposes of achieving a smaller prophylactic device. The approach described in the '319 patent uses the MVT therapy to provide a smaller and less expensive implantable device that can maintain some cardiac output without necessarily providing defibrillation therapy.

Unlike a conventional defibrillator or an ICD, which operates with the primary purpose of restoring a normal cardiac rhythm, MVT stimulation can be used to provide cardiac output, which in turn causes perfusion of the heart and brain, as well as other critical body tissues. By providing perfusion of the heart and other vital organs, MVT prolongs the life of the patient even while the patient continues experiencing the arrhythmia. Additionally, MVT improves the likelihood of successful defibrillation or of a spontaneous return of circulation. An AED equipped with MVT can provide consistent high quality chest compressions. In the case of an implanted ICD, backup chest compressions provided by MVT can, in one sense, be even more important than in an external, since in the case of the implantable device there may be no rescuer available to perform CPR when needed.

A number of challenges remain in practically incorporating MVT into defibrillation devices. As heretofore envisioned, a combined defibrillation-MVT device utilizes separate defibrillation and MVT circuitry for generating and applying each type of electrotherapy since the magnitudes of these treatments can differ by an order of magnitude or more. Thus, improvements to a combined defibrillation—MVT device would be desirable.

SUMMARY OF THE INVENTION

One aspect of the invention is directed to a multi-modal electrotherapy apparatus for treating a patient experiencing an arrhythmia. The two modes of electrotherapy include medium voltage therapy (MVT) and defibrillation. The MVT has energy and waveform characteristics to force repeated mechanical compression of the patient's heart that causes hemodynamic perfusion in the patient; the defibrillation therapy has energy and waveform characteristics to defibrillate the heart.

A low-voltage power source, such as a battery, is adapted to supply energy for operation of the apparatus. A high-voltage energy storage circuit, such as a bank of capacitors, is adapted to store energy at a high voltage level sufficient for administering defibrillation therapy to the patient. Notably, the high-voltage energy storage circuit is also adapted to store energy for administering MVT.

A charging circuit has an input electrically coupled to the low-voltage power source and an output electrically coupled to the high-voltage energy storage circuit. The charging circuit is configured to transfer energy from the low-voltage power source to the high-voltage energy storage circuit while increasing the voltage at the input to the high voltage level at the output according to charging control signaling. A discharge circuit is electrically coupled to the high-voltage energy storage circuit and to patient terminals. The discharge circuit is adapted to switchably connect and disconnect the high-voltage energy source with the patient terminals according to discharge control signaling.

Control circuitry is electrically coupled to the discharge circuit and configured to provide the charging control signaling and discharge control signaling. The control circuitry is further configured to initiate charging of the high-voltage energy storage circuit, provide discharge control signaling to cause the discharge circuit to apply MVT from the high-voltage energy source to the patient via the patient terminals prior to completing charging of the high-voltage energy storage circuit to the high voltage level and, in response to charging of the high-voltage energy storage circuit to the high voltage level, provide discharge control signaling to cause the discharge circuit to administer defibrillation therapy from the high-voltage energy source to the patient via the patient terminals.

In another aspect of the invention, an improved multi-modal electrotherapy apparatus has circuitry for administering defibrillation therapy and for administering MVT as a distinct therapy from cardioversion and pacing therapies to force compression of the heart. The improvement includes a combined-use bank of at least one capacitor for storing energy to be administered as defibrillation therapy and MVT. Combined-use discharge circuitry is electrically coupled between the combined-use bank of at least one capacitor and patient terminals for selectively administering energy from the bank of at least one capacitor according to a plurality of controllable waveforms as either defibrillation therapy or MVT. A controller electrically coupled to the combined-use discharge circuitry is configured to cause the discharge circuitry to apply the MVT from the bank of at least one capacitor while the bank of at least one capacitor undergoes charging in preparation for administration of the defibrillation therapy.

In another aspect of the invention, the improvement entails a combined-use bank of at least one capacitor for storing energy to be administered as defibrillation therapy and MVT; combined-use discharge circuitry electrically coupled between the combined-use bank of at least one capacitor and patient terminals for selectively administering energy from the bank of at least one capacitor according to a plurality of controllable waveforms as either defibrillation therapy or MVT; and a controller electrically coupled to the combined-use discharge circuitry and configured to cause the discharge circuitry to administer the defibrillation therapy within 5 seconds after administration of the MVT from the bank of at least one capacitor.

A further aspect of the invention is directed to a method for administering medium-voltage therapy (MVT) to a patient experiencing an arrhythmia. According to the method, a charge storage circuit, such as a capacitor, is charged. While charging the charge storage circuit, the charge storage circuit is switchably connected and disconnected across patient terminals to produce packets of MVT current pulses. These pulse widths between 150 microseconds and 10 milliseconds and pulse periods of between 5 milliseconds and 70 milliseconds. While connecting and disconnecting the charge storage circuit across the patient terminals, pulse parameters of each pulse of the packets of pulses are varied such that at least one parameter from among the pulse width and pulse amplitude is adjusted approximately in inverse proportion to changes in a voltage of the charge storage circuit. In the present context, the term approximately means that variations from the ideal inverse proportion are possible, but negligible in a therapeutic sense.

A number of advantages will become apparent from the following Detailed Description of the Preferred Embodiments.

BRIEF DESCRIPTION OF THE DRAWINGS

The invention may be more completely understood in consideration of the following detailed description of various embodiments of the invention in connection with the accompanying drawings, in which:

FIGS. 2A-2C illustrate various examples of electrode arrangements for implantable MVT devices such as the device of FIG. 1 according to various embodiments.

Figure 1:
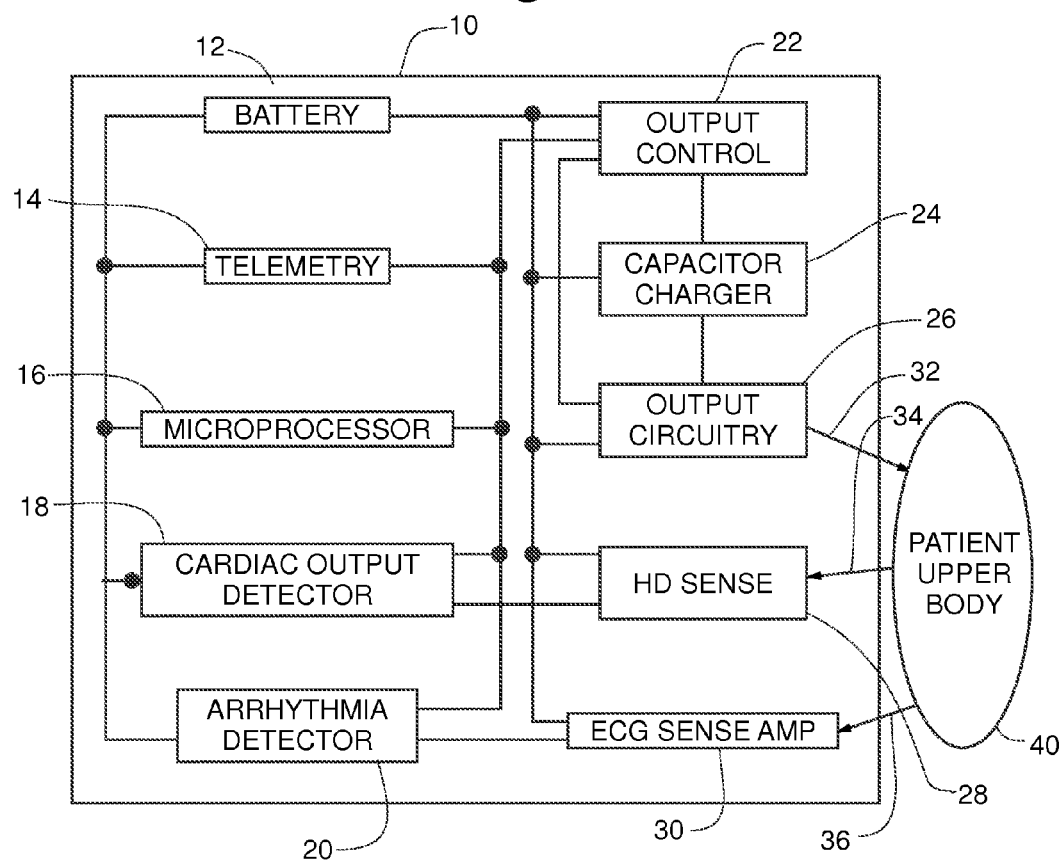
FIG. 1 is a diagram illustrating the sub-systems of an implantable device enabled with medium voltage therapy (MVT) facilities, according to one embodiment.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE PREFERRED EMBODIMENTS

Aspects of the invention are directed to apparatus and methods for applying electrotherapy to treat one or more types of arrhythmias in a patient. The electrotherapy is automatically applied by a device, either implantable or external to the patient that provides electrotherapy of at least two modalities: defibrillation therapy, and medium voltage therapy (MVT). Defibrillation therapy involves the use of high-voltage pulses fully reset the electrical activity within the heart, after which a normal sinus rhythm can be restored (without re-entrant activity of propagating action potential waves).

MVT involves stimulation of muscle cells in the heart, elsewhere in the upper body, or both, so that those muscle cells are forced to contract and relax repeatedly in a controlled manner. To force each contraction, MVT is of a sufficient charge level and pulse rate to overwhelm the body's natural control of these muscles to force the contraction of relaxed (i.e. non-captured) muscle cells while maintaining already captured muscle cells in their contracted states.

Insofar as heart muscle is concerned, MVT can be said to directly capture a substantial portion of myocardial cells, throughout the heart, rather than rely on a working natural mechanism of propagating waves of action potentials. MVT differs considerably from pacing therapy in this regard. Pacing involves applying a small stimulus to a specific part of the heart, to trigger a somewhat naturally-propagating wave of action potentials. Instead, MVT applied to heart muscle does not rely on a working mechanism of action potential propagation. In MVT, myocardial cells throughout the heart, (though not necessarily all of the myocardium) are captured at the same time as a burst of MVT charge is applied to those cells, forcing the captured muscle cells to contract simultaneously (i.e., not in a sequence as is the case with a natural sinus rhythm or in response to a pacing pulse). A sufficient quantity of cells is captured by MVT to produce a positive hemodynamic effect that is similar to what may be achieved in a CPR-type chest compression.

MVT also differs from cardioversion, which involves administering a single and closely-timed short-duration electrical shock to the heart during the R wave of the QRS complex, to terminate arrhythmias such as atrial fibrillation or ventricular tachycardia by momentarily interrupting the abnormal rhythm, allowing the heart's natural electrical system to regain normal control of the heart. Cardioversion pulses can be monophasic or biphasic, and each electrical pulse is applied once during each ECG cycle with a duration on the order of milliseconds and generally only once per arrhythmia. MVT does not require there to be a discernable rhythm in the ECG to which the pulses must be synchronized. Also, MVT is applied in bursts of pulses, referred to herein as pulse trains, that are sustained for a much longer duration so that the captured muscle tissue is held in its contracted state, then released to relax, then again captured and maintained contracted. The purpose of MVT is not to reset the electrical activity of the heart; rather it is to force mechanical contractions without regard to whether the heart has a working electrical system capable of propagating waves of action potentials.

MVT applied to non-cardiac muscle, such as skeletal musculature, diaphragm, etc., causes contraction of these muscle tissues and mimics the effect of CPR-type chest compressions. Thus, MVT can contract the heart not only by directly capturing myocardial cells to electrically force their contraction, but also by electrically forcing non-cardiac cells in muscle tissue surrounding the heart to contract, thereby reducing the volume in the chest and mechanically compressing the heart.

MVT can therefore be used to cause perfusion of at least the heart, and preferably also the lungs, brain, and other critical organs, to prolong the life of a patient during a hemodynamically-compromising arrhythmia in which there is insufficient cardiac output to naturally sustain the life of the patient.

FIG. 1 is a block diagram illustrating an implantable combined defibrillation-MVT device 10 constructed in accordance with one aspect of the invention. The device circuitry is electrically coupled with regions of the patient's upper body 40 via a series of leads—output lead 32, pressure sense lead 34, and ECG sense lead 36. The electronic circuit includes a conventional ECG amplifier 30 for amplifying cardiac signals. The amplified cardiac signals are analyzed by a conventional arrhythmia detector 20 that determines if an arrhythmia is present. The arrhythmia detector 20 may be one of several types well known to those skilled in the art and is preferably able to distinguish between different types of arrhythmias, for example; fibrillation, tachycardia, and asystole.

Optionally, the exemplary circuit contains a hemodynamic sensing section 28 which amplifies and conditions a signal from a one or more hemodynamic sensors such as, for example, a pressure sensor, a microphone, an ultrasonic blood flow sensor, an impedance plethysmography device, a pulse oximeter, a cardiac impedance sensor, or the like. The output of the hemodynamic sense circuit 28 is fed to a cardiac output detection circuit 18 that analyzes the data and determines an estimate of the cardiac output. Data from the arrhythmia detector circuit 20 and the cardiac output detection circuit 18 is fed to the microprocessor 16. This combination of inputs gives the ability to sense PEA as PEA is defined as the lack of cardiac output in the presence of otherwise normal heart rates. An aspect of this invention is the use of the following algorithm:

1. If there is no cardiac output found from hemodynamic sensors then
2. Check the heart rate via the arrhythmia detector and
3. If the arrhythmia detector does not detect an arrhythmia then
4. Declare the presence of pulseless electrical activity (PEA)
5. Deliver PEA therapy The microprocessor 16 determines if electrotherapy is appropriate, and what modality of the electrotherapy to apply at what time, i.e., defibrillation shock or MVT. Typically, MVT is applied close in time prior to application of the defibrillation shock. In one such embodiment, the defibrillation shock is applied within 30 seconds following cessation of the MVT. In a related embodiment, the time period between cessation of the MVT and the defibrillation is reduced to about 10 seconds. In a further embodiment, the time period between the cessation of the MVT and the application of the defibrillation is less than 5 seconds (e.g., 3 seconds). In another type of embodiment, the time period between cessation of MVT and application of the defibrillation shock is reduced to less than one second.

When electrotherapy is indicated, the microprocessor 16 prompts the output control 22 to charge a capacitor within the output circuit 26 via the capacitor charger 24. The output control 22 directs the output circuitry 26 to deliver the electrotherapy to the patient's upper body regions 40 via the output leads 32. Notably, according to one aspect of the invention, the capacitor charger 24 and output circuitry 26, including the capacitor, are used for preparing (i.e., charging) and applying both MVT and defibrillation electrotherapies. In a related aspect of the invention, the MVT can be administered while the capacitor charger 24 circuit prepares for administration of the defibrillation therapy.

The microprocessor 16 may communicate with external sources via a telemetry circuit 14 within the device 10. The power for the device 10 is supplied by an internal battery 12.

FIG. 2A is a diagram showing the connection of an implantable device 10' according to one embodiment to the heart as one of the regions in the patient's upper body 40 in an epicardial patch configuration. In this thoracotomy configuration, current passes through an output lead pair 32 to electrode patches 42 which direct the current through the heart. A pressure sense lead 34 passes the signal from an optional pressure transducer 46 that enables a measurement of blood pressure. The ECG is monitored by sense electrodes 44 and passed to the device 10' by a lead 36. In an example embodiment, the area of the electrodes 42 is between approximately 0.5 cm$^2$ and 20 cm$^2$ each.

FIG. 2B illustrates an example of a non-thoracotomy arrangement according to one embodiment. In this system, the current passes from a coil electrode 52 in the heart to the housing of the MVT device 10". An endocardial lead 50 combines the ECG sensing lead and the pulse output lead. The ECG is monitored by sense electrodes 44 in the heart and passes through the endocardial lead 50. There is an optional pressure transducer 46 that in one embodiment may be positioned in the heart, that passes a signal to the device 10" via optional lead 34.

Figure 2C:
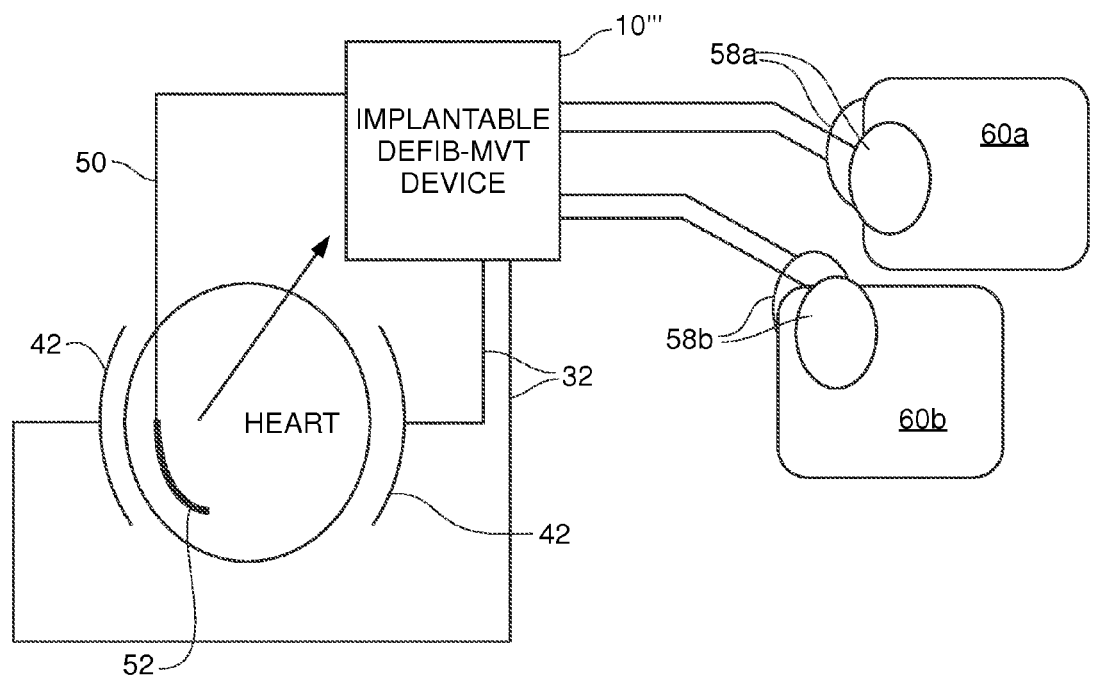

FIG. 2C illustrates an implantable MVT device 10''' that supports a set of diverse electrode arrangements for selectively applying MVT to different areas of the patient. In addition to electrodes 42 and 52 discussed above in the thoracotomy and non-thoracotomy arrangements for directing defibrillation pulses and MVT through the myocardium, device 10''' further includes additional electrodes 58a and 58b for placement at specific locations in the patient's upper body, 60a and 60b, to direct MVT through non-cardiac muscles. Examples of locations 60a and 60b include (without limitation) locations for activating the pectoral muscles, intercostal muscles, the diaphragm (e.g., via stimulation of the phrenic nerve), and the abdominal muscles. The additional electrodes 58a and 58b, in various embodiments, have a variety of constructions and locations, including, for example, subcutaneous patch electrodes, one or more additional electronics/battery housings, intra-vascular leads, and the like. Placements include any suitable location such as, for example, subcutaneously at the base of the neck, in the azygos vein, in the cephalic vein, subcutaneously in the lower torso, and subcutaneously on one or both sides of the upper torso. In a related embodiment, the additional one or more of electrodes 58a and 58b are used for hemodynamic measurements such as, for example, electrical impedance plethysmography.

Figure 3:
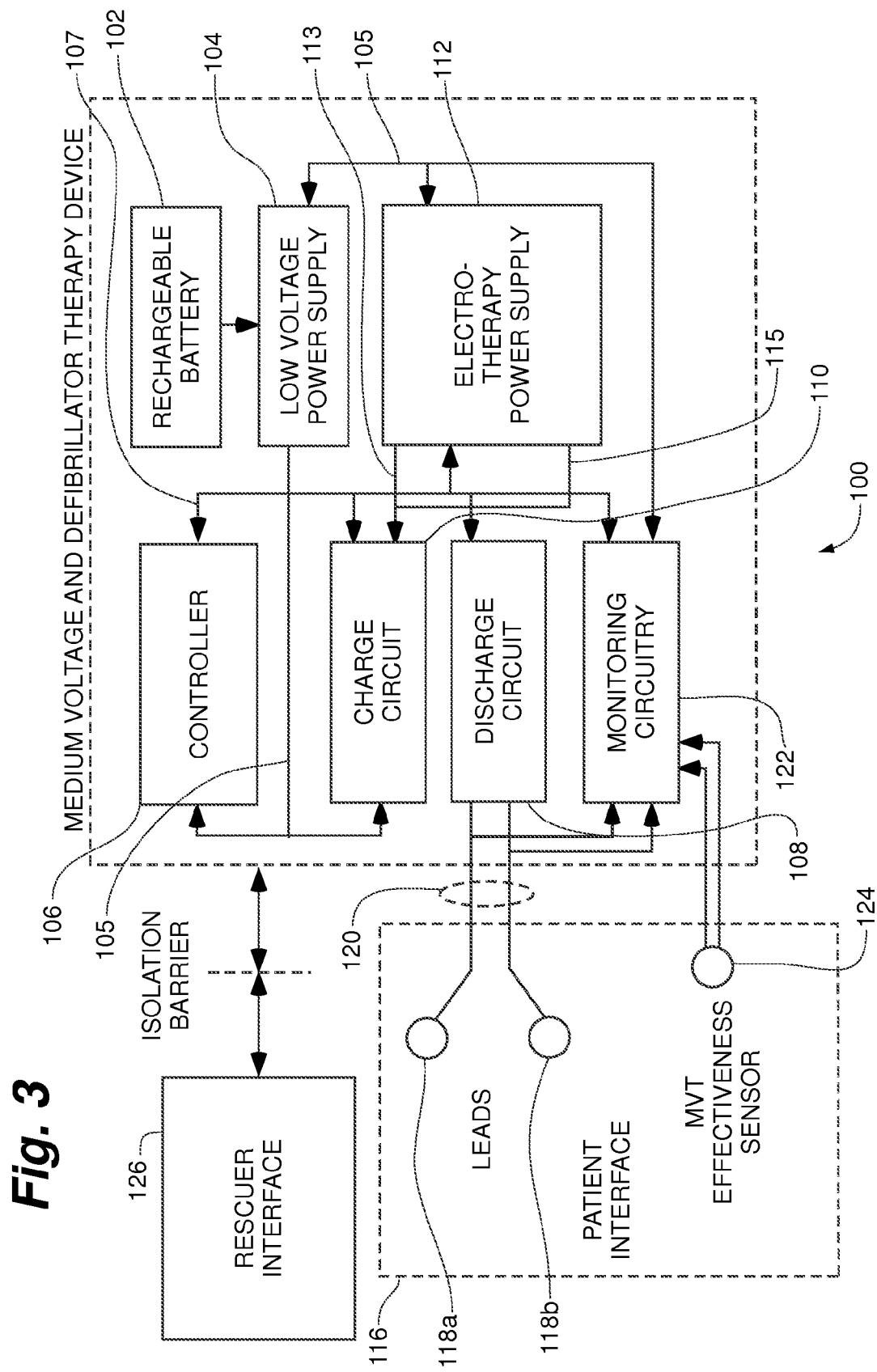
FIG. 3 is a diagram illustrating the sub-systems of an external device enabled with medium voltage therapy facilities, according to one embodiment.

FIG. 3A is a diagram illustrating an example AED 100 that utilizes MVT according to one embodiment. AED 100 can be a hand-portable instrument that is self-powered from an optionally-rechargeable battery 102. Battery 102 provides an energy source that can be converted and conditioned for powering the various circuitry of AED 100. A low voltage power supply 104 converts the battery power into one or more stabilized power supply outputs 105 for supplying the power to the subsystems of AED 100. The subsystems include a controller 106, for example a microprocessor that is programmed and interfaced with other subsystems to control most of the functionality of AED 100.

In the embodiments in which the controller 106 is implemented as a microprocessor or microcontroller, the microprocessor interface includes data and address busses, optional analog and/or digital inputs, and optional control inputs/outputs, collectively indicated at microprocessor interface 107. In one example embodiment, the microprocessor is programmed to control the sequence of the electrotherapy, as well as the output waveform parameters. The user input to the system can be in the form of simple pushbutton commands, or voice commands.

Example AED 100 includes a discharge circuit 108 for administering therapeutic stimuli to the patient. Discharge circuit 108 controls the release of therapeutic energy, in either the defibrillation, or MVT modalities, to achieve a desired stimulus having a particular waveform. Charge circuit 110 energizes discharge circuit 108 to achieve the desired output stimulus. Electrotherapy power supply 112 provides a sufficient energy source 113 to charge circuit 110 to enable charge circuit 110 and discharge circuit 108 to ultimately deliver one or more defibrillation pulses, and to deliver MVT, to an exterior surface of the patient.

Typically, a voltage sufficient to achieve a therapeutic defibrillation stimulus from the exterior of a patient is in the range of 1 kV-3 kV; whereas the typical range of voltages for externally-applied MVT is 100-1000 V. Notably, according to one aspect of the invention, charge circuit 110 and discharge circuit 108, are utilized for both modalities. In a related aspect of the invention, the MVT can be administered while the charge circuit 110 prepares for administration of the defibrillation therapy.

The defibrillation and MVT stimuli are administered to the patient via patient interface 116. In one embodiment, patient interface 116 includes electrodes 118a and 118b that are adhesively applied to the patient's chest area, typically with an electrically-conductive gel. Electrodes 118a and 118b are electrically coupled, such as by insulated copper wire leads 120, to discharge circuit 108. In one example embodiment, electrodes 118a and 118b can deliver the defibrillation stimuli and the MVT stimuli as well as obtain information about the patient's condition. For example, electrodes 118 can be used to monitor the patient's cardiac rhythm. Signals originating in the patient that are measured by electrodes 118 are fed to monitoring circuitry 122.

In one embodiment, patient interface 116 includes an MVT effectiveness sensor 124 coupled to monitoring circuitry 122. MVT effectiveness sensor 124 can measure observable patient characteristics that are related to the patient's condition, in like fashion to the hemodynamic monitoring and determining arrangements described above for an implantable embodiment.

AED 100 also includes a rescuer interface 126 operatively coupled with controller 106. In one embodiment, rescuer interface 126 includes at least one pushbutton, and a display device for indicating at least the operational status of AED 100. In a related embodiment, rescuer interface includes a system for providing visual or audible prompting or instructions to the rescuer. In another embodiment, rescuer interface 126 includes a plurality of human-operable controls for adjusting the various AED operational parameters, and a display device that indicates measurements made by monitoring circuitry 122.

Figure 4:
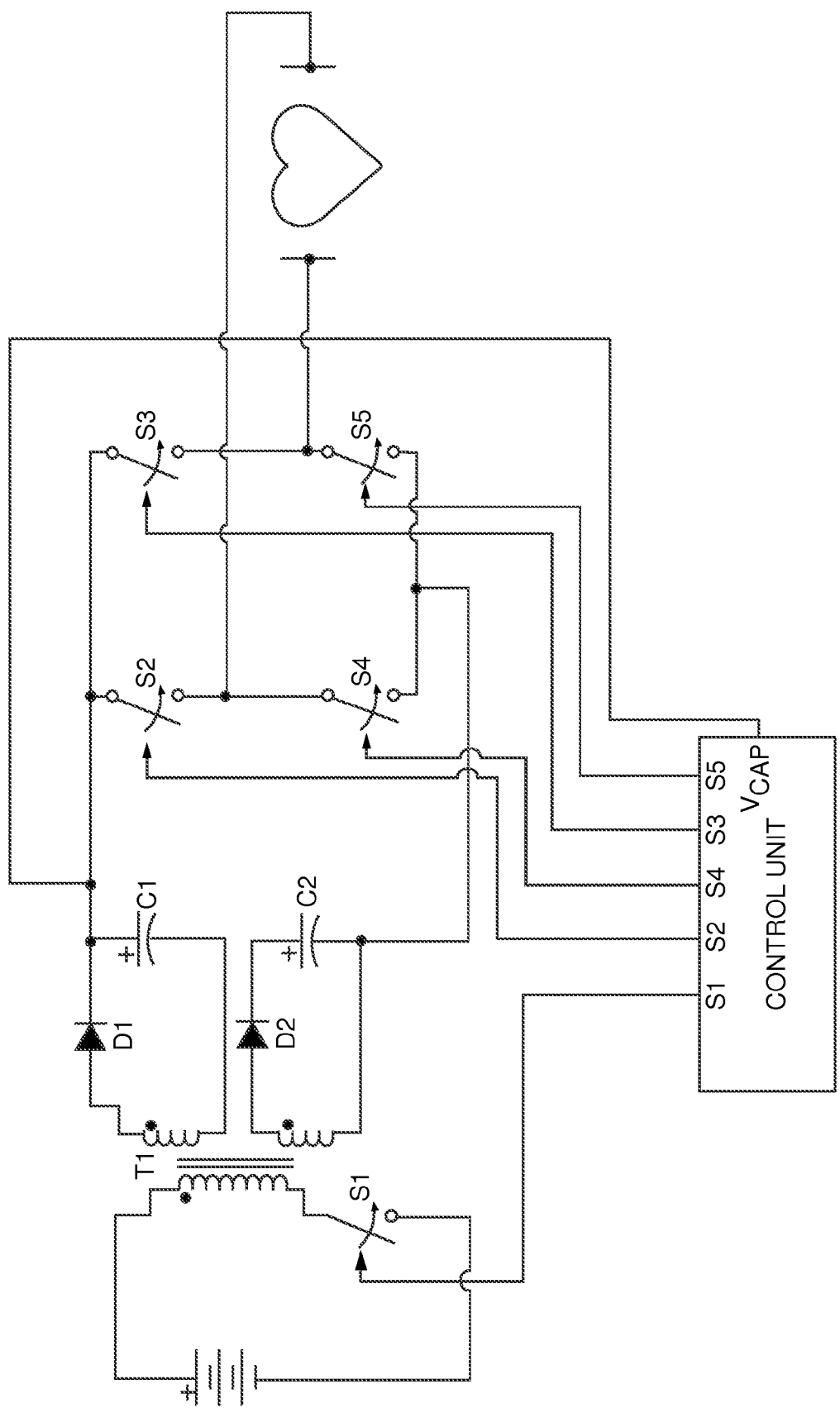
FIG. 4 is a simplified circuit diagram depicting the primary components of an exemplary charging and discharging circuit according to one embodiment.

FIG. 4 is a simplified circuit diagram depicting the primary components of an exemplary charging and discharging (i.e., output) circuit according to one embodiment. This type of charging and discharging circuit is applicable in either the implantable device or the external AED embodiments. In the simplified charging portion, battery B1 supplies current to the primary winding of transformer XMFR1 while switch S1 is operated in a periodic switching mode by the control unit. In each switching cycle, after switch S1 has been on sufficiently long to magnetically charge transformer XMFR1, switch S1 is opened. The primary side of the transformer XMFR1 is magnetically coupled to the secondary windings and, by a turns ratio of n:m (with m being a multiple of n), the secondary side of transformer XMFR1 increases the voltage from the primary side. By the principle of conservation of energy, the energy delivered into the primary side of transformer XMFR1 must go some place and in this circuit it flows through diodes D1 and D2 to charge capacitors C1 and C2. For the sake of simplicity, several components unrelated to the basic functionality are omitted, such as a snubber network for absorbing voltage spikes produced by the primary winding when the switch S1 is opened. This type of charging circuit is well known in the art, as are a variety of adaptations, any of which may be suitable according to various embodiments. Other types of charging circuits may also be utilized, such as boost converters, charge pumps, etc. Notably, this charging circuit boosts voltages for both, the defibrillation energy, and the MVT.

The capacitive storage for the shock is depicted in FIG. 4 as a network of 2 capacitors in this schematic for simplicity. In a more practical embodiment, the system is realized with a set of 3-7 capacitors in series with suitable interconnections with the charging and discharging circuitry. Hereinafter, the capacitor bank may be referred to as simply, the "capacitor."

The discharge portion of this exemplary circuit is an H-bridge topology. Switches S2-S5 can be implemented utilizing suitable technology such as, for instance, solid state devices like FET devices, IGBT devices, SCR devices, and the like. In this simplified diagram, a number of components are omitted for the sake of brevity, as this H-bridge circuit topology is well-known. For instance, isolated driving circuits are generally used for controlling the upper H-bridge switches S2 and S3. Also, an anti shoot-through provision is generally employed to prevent both switches of a common leg of the H-bridge from being in their conductive states at any moment.

The control unit comprises one or more control circuits such as at least one microprocessor systems. In an example embodiment with multiple distinct control circuits, a first control circuit controls a switching regulator that operates switch S1 in the charging circuit, whereas a second control circuit controls switches S2-S5 in the discharge portion of the circuit. These distinct control circuits can be distributed As depicted, there can be at least one closed-loop feedback arrangement, such as the measurement of the capacitor voltage Vcap, which the control unit uses to adjust the operation of the charging and discharging circuitry.

In operation, to deliver a biphasic defibrillation shock according to an exemplary embodiment, upon charging up of the capacitor to a suitable voltage for defibrillation, switches S2 and S5 are enabled for a period of time between 3 and 8 ms to deliver the positive phase to the chest (or directly to the heart in the case of an implantable device). Immediately afterwards, switches S2 and S5 are turned off by the control unit and switches S3 and S4 are enabled to a deliver a negative phase for approximately 3-4 ms.

For the delivery of a MVT pulse train according to an exemplary embodiment, switches S2 and S5 are turned on briefly to deliver a single pulse, then one or both of these switches is turned off. There is a delay until the start of the next individual pulse, then the next pulse is delivered in the same manner (i.e. conducting current through switches S2 and S5).

Figure 5A:
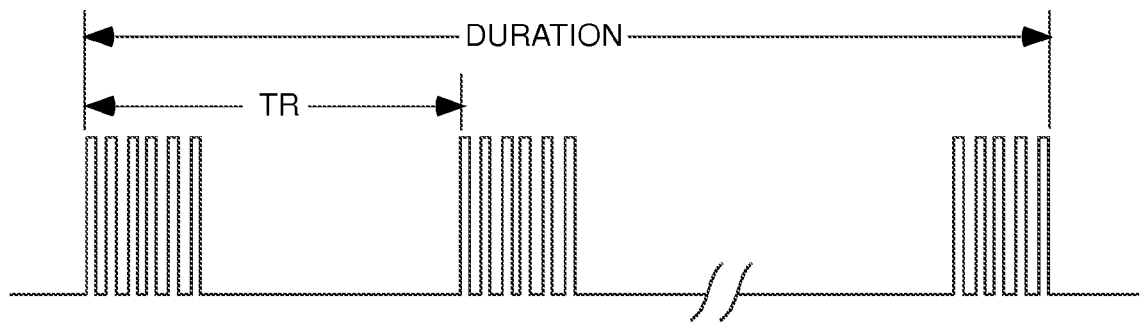
FIGS. 5A and 5B are waveform diagrams illustrating various conventional MVT parameters.
Figure 5B:
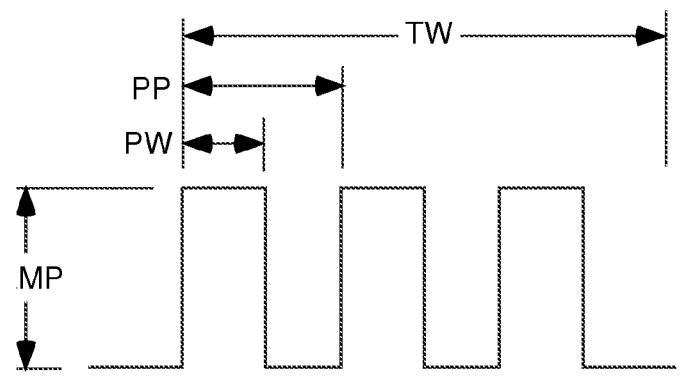

Conventional MVT waveforms are illustrated in FIGS. 5A and 5B. MVT therapy is composed of a plurality of pulse trains that are administered periodically for a treatment duration, as illustrated in FIG. 5A. The pulse trains are applied with a periodicity that can be expressed as a train rate TR. Pulse trains are composed of a predetermined number of individual pulses separated by an inter-pulse time duration. Each pulse train has a train width TW, as illustrated in FIG. 5B. The individual pulses inside the pulse train have a Pulse With PW. The pulses have a periodicity that can be expressed a pulse period PP.

For MVT, Table 1 below provides an exemplary range of parameter values corresponding to empirically determined effectiveness.

TABLE 1

Exemplary Parameter Value Ranges for MVT

| Parameter | Value of Parameter (Implanted Devices) | Value of Parameter (External Devices) |
| --- | --- | --- |
| MVT Duration | 5-120 s | 5-120 s |
| Train Rate | 30-160 per min. | 30-160 per min. |
| Pulse Current Amplitude | 0.25-5 A | 0.25-5 A |
| Pulse Voltage Amplitude | 15-250 V | 60-300 V |

TABLE 1-continued

Exemplary Parameter Value Ranges for MVT

| Parameter | Value of Parameter (Implanted Devices) | Value of Parameter (External Devices) |
|---|---|---|
| Pulse Width | 0.15-10 ms | 0.15-10 ms |
| Pulse Period | 5-70 ms | 5-70 ms |

The MVT waveform can be further tuned to increase selectivity of muscle type in the application of the MVT. Muscle type selectivity permits more precise targeted treatment based on the patient's condition, and facilitates management of muscle fatigue to prolong the MVT treatment duration.

An MVT waveform that is optimized for skeletal muscle capture (OSC) according to one embodiment is adapted to force primarily skeletal muscle contractions. The OSC waveform is adapted to force a contraction and subsequent release of skeletal muscles in order to achieve perfusion of the heart and other vital organs, and can force some amount of ventilation.

An MVT waveform that is optimized for myocardial capture (OMC) according to a related embodiment is adapted to force cardiac muscle contractions. The OMC waveform is adapted to force contraction of primarily cardiac muscles in order to achieve some level of perfusion for the heart and other vital organs. Tables 2 and 3 below provide exemplary ranges for OMC and OSC MVT parameter values; whereas tables 4 and 5 that follow provide an exemplary optimal set of values for OMC and OSC waveforms, respectively.

TABLE 2

Exemplary Stimulation Waveform for OMC

| Variable Parameter | Optimal Range |
|---|---|
| Pulsed Output Voltage | 75-300 V (external); 20-80 V (implantable) |
| Pulsed Output Current | 1-5 A |
| Pulse Width | 5-10 ms |
| Pulse Period | 10-20 ms |
| Duration | 10-30 seconds |
| Packet Width | 100-300 ms |
| Train Rate | 80-160 bpm |

TABLE 3

Exemplary Stimulation Waveform for OSC

| Variable Parameter | Optimal Range |
|---|---|
| Pulsed Output Voltage | 75-300 V (external); 20-80 V (implantable) |
| Pulsed Output Current | 1-5 A |
| Pulse Width | 0.10-0.25 ms |
| Pulse Period | 20-40 ms |
| Duration | 10-30 seconds |
| Packet Width | 100-300 ms |
| Train Rate | 80-160 bpm |

TABLE 4

Exemplary Stimulation Waveform for OMC

| Variable Parameter | Optimal Value |
|---|---|
| Pulsed Output Voltage | 75-300 V (external); 20-80 V (implantable) |
| Pulsed Output Current | 2 A |
| Pulse Width | 7.5 ms |
| Pulse Period | 15 ms |
| Duration | 20 seconds |
| Packet Width | 200 ms |
| Train Rate | 120 bpm |

TABLE 5

Exemplary Stimulation Waveform for OSC

| Variable Parameter | Optimal Value |
|---|---|
| Pulsed Output Voltage | 75-300 V (external); 20-80 V (implantable) |
| Pulsed Output Current | 2 A |
| Pulse Width | 0.15 ms |
| Pulse Period | 30 ms |
| Duration | 20 seconds |
| Packet Width | 200 ms |
| Train Rate | 120 bpm |

Notably, in this conventional MVT waveform the width of the individual pulses in the pulse trains are constant, and the pulse amplitude for each of the individual pulses is generally constant. According to one aspect of the invention, as described above, the same charging, energy storage, and discharging circuit are used for the MVT as for the defibrillation therapy. In this type of electrotherapy, it is important to stimulate the patient with MVT just before applying defibrillation therapy. Stated another way, it is important to apply the defibrillation very soon after cessation of MVT. This presents a challenge in that it generally takes a considerable amount of time to charge the capacitors to a defibrillation-level voltage—on the order of 5-30 seconds or more for devices using efficient and practical charging circuits (e.g. 20-25 watt charging circuit for an external device and a 6-12 watt charging circuit for an implantable device charging to 360 J or 45 J). Notably, the charge times are longer than those suggested by a simple division of the energy by the charging power since the electrolytic capacitors have substantial leakage when their voltage approaches the maximum. I.e. a 20 watt charger will charge an external defibrillation capacitor to 40 J in 2 seconds (=40÷20). However, charging to the maximum 360 J requires more time than 18 seconds (=360÷20) due to this nonlinear leakage effect.

Figure 6:
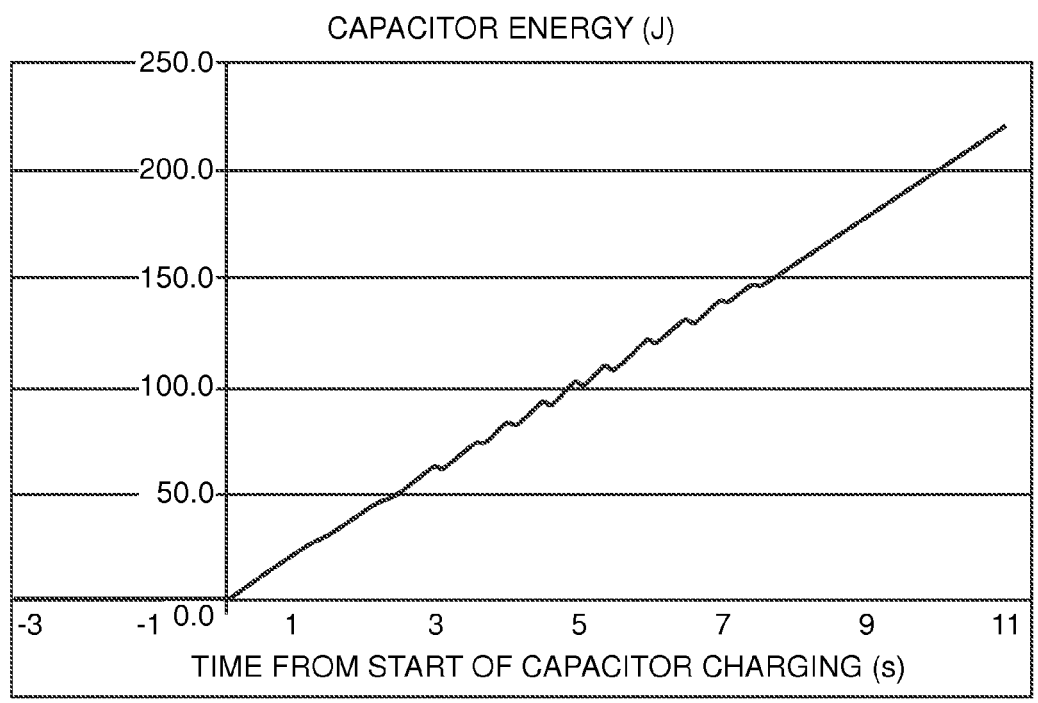
FIG. 6 illustrates how the capacitor energy increases with time according to an implementation in one type of embodiment in which MVT is applied during charging of the capacitor.

FIG. 6 illustrates how the capacitor energy increases with time according to an implementation in one type of embodiment. This example is based on a typical 22-watt charging circuit, which is typical for an external defibrillator, and a 200-joule delivered shock, which is also typical. An implantable cardioverter-defibrillator (ICD) has a charging circuit capable of typically 6-12 watts. Thus, in the case of an ICD, the shape of the capacitor charging energy would be the same but the final energy will be lower—on the order of 40 joules.

According to one aspect of the invention, the MVT waveform is adapted so that MVT according to certain embodiments described herein, which is therapeutically equivalent to the therapy provided by the conventional MVT waveform, is delivered from the energy storage capacitor while the capacitor is charging to a higher defibrillation therapy voltage. In a conventional defibrillator, the capacitor energy increases approximately linearly with time (due to increasing leakage in the capacitor, this curve is not completely linear, but that issue has no bearing here). In the plot of FIG. 6, for the embodiment represented, several small stair steps, or nibbles, are visible during the first 7.5 seconds. That is due to the fact that energy from the charging circuit is being used to deliver MVT to the patient. The nibbles are smaller at the beginning of the charging due to the fact that the MVT pulses are more energy efficient at the beginning while the nibbles get larger near the top as will be explained later. From 7.5 seconds on, there is no stepping in this embodiment as 100 percent of the charging energy is being devoted to "topping off" the main defibrillation shock capacitor.

According to one embodiment, MVT pulses are administered for a pulse width PW that produces a similar amount of charge transfer to the patient as a therapeutically similar conventional MVT waveform. In one embodiment, constant charge is maintained in the MVT pulses by adjusting the pulse width PW as the capacitor voltage changes. Thus, as the capacitor voltage increases due to charging, the pulse width is progressively reduced for successive pulses so that each pulse delivers approximately as much charge to the patient.

Figure 7:
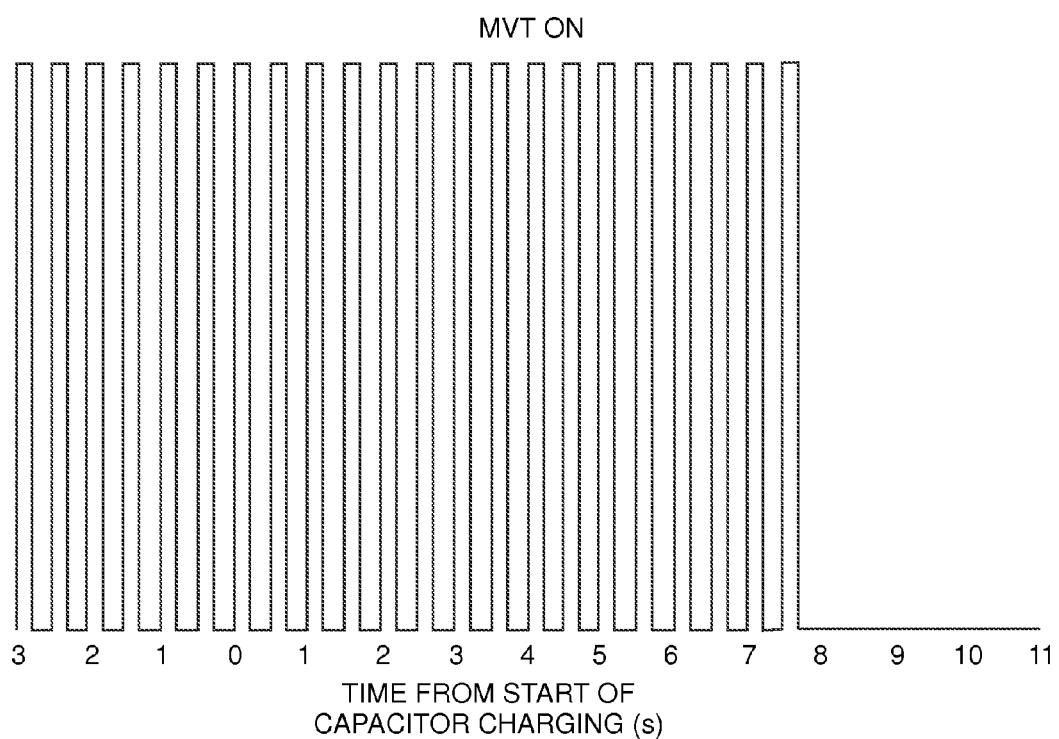
FIG. 7 illustrates timing of the MVT pulse trains while the main capacitor undergoes charging according to one example embodiment.

FIG. 7 illustrates the timing of the MVT pulse trains while the main capacitor undergoes charging according to one example embodiment. In the example illustrated here, the MVT is applied for a period of 60-120 seconds before the defibrillation shock is given. The chart in FIG. 7 is a chart that illustrates a portion of this period. In the chart, the time range prior to time 0 represents a period in which the capacitor is already charged up to an initial MVT-level voltage that is insufficient to defibrillate the heart but sufficient to administer MVT. This voltage during the first period is held for some time until the device determines that it is time for the capacitor to be charged further to prepare for administering defibrillation therapy. During this first period, the voltage on the capacitor is not changing appreciably, so MVT can be applied in conventional fashion.

After time 0 as shown in FIG. 7, the MVT pulse trains are delivered for a second period of time while the capacitor charges to the level called for to defibrillate the heart. This period of time can last from between several seconds to several tens of seconds, depending on the time required to charge the capacitor for defibrillation. Notably, the ability to deliver MVT during charging of the capacitor can allow the device to utilize a lower-wattage charging circuit, which may be particularly useful in implantable devices where size and energy conservation are particularly important design criteria. This is because administration of the MVT prior to defibrillation offers a benefit associated with delaying the administration of defibrillation; thus, the capacitor in a MVT-enabled device does not need to be charged for defibrillation as quickly as the capacitor of a device without MVT (or without the ability to administer MVT during charging of the capacitor for defibrillation).

Just prior to administration of the defibrillation shock, the MVT is ceased. Depending on the capabilities of the discharging circuit according to various embodiments, the time between cessation of MVT and administration of the defibrillation shock is between about 5 seconds and under one second. In one particular embodiment, this time period is about 3 seconds. This is a substantial advantage over other methods of delivering CPR, in that the gap between the end of the last chest compression and the delivery of the shock is on the order of only a few seconds. This is far smaller than the gap that is seen with manual chest compressions before the shock due to the operator fears of being of shocked and the timing requirements for pushing the defibrillator shock button.

Figure 8:
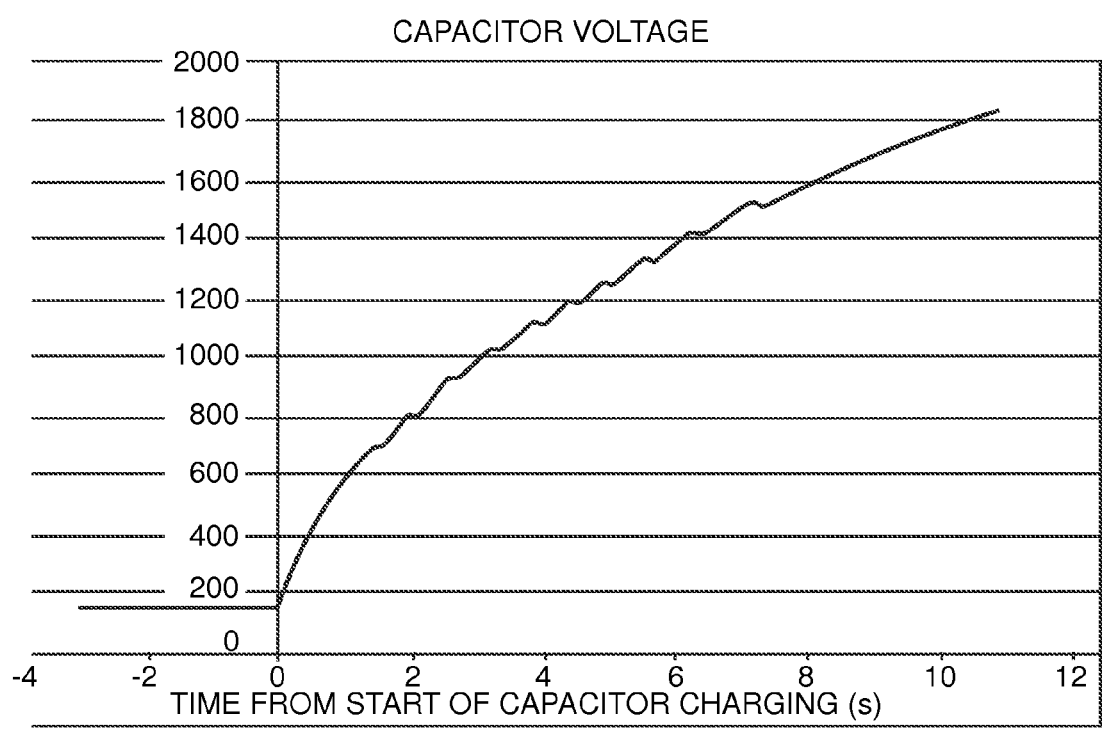
FIG. 8 is a chart depicting the capacitor voltage in an embodiment that applies MVT during charging for defibrillation.

FIG. 8 is a chart depicting the capacitor voltage in an embodiment that applies MVT during charging for defibrillation (note that this ignores the charge slowing at the peak voltage due to capacitor leakage). Since the energy in a capacitor is proportional to the voltage squared, the voltage curve is basically a square root function of the time. In this example, the curve is not a precise square root function since the voltage is precharged to 150 volts at time 0 before the capacitor begins to further charge in preparation to deliver defibrillation therapy. In this example, prior to time 0 the capacitor is maintained at 150 volts throughout the delivery of the MVT by running the charging circuit intermittently. When it is time to charge a capacitor up to its full voltage for the defibrillation shock, the capacitor has a small "head start" on the voltage since it is beginning at 150 V. Note that the stair steps stop at 7.5 seconds and the capacitor is of sufficient voltage to deliver its shock at about 10.5 or 11 seconds. In this embodiment, there is a short delay on the order of 3 seconds from the end of the MVT to the delivery of the defibrillation shock.

More generally, the voltage on the capacitor during charging while applying MVT according to one embodiment can be approximately represented mathematically as follows:

In short pulse range (d<50 μs) the required charge q is fairly constant. Also, assume constant charging power P. The following symbols are utilized in the expressions that follow:

E=capacitor energy
C=capacitance of capacitor
V=voltage on capacitor
R=resistance of shock path
t=time into charging cycle
f=train rate in pulses per second $$E = Pt$$

$$= \tfrac{1}{2}CV^2$$

$$V = (2Pt/C)^{1/2}$$

For constant charge:

$$q = Vd/R$$

hence, $$d = qR/V$$

for the pulse duration. Hence $$d = qR\sqrt{\frac{C}{2Pt}}.$$

Energy per pulse is then given by:

$$E = \frac{dV^2}{R} = \left[\frac{qR}{V}\right]\left[\frac{2Pt}{C}\right]\left[\frac{1}{R}\right]$$
$$= 2qPt/C$$

Hence, the average power lost to the MVT nibbles is:

$$P' = Ef = 2fqPt/C.$$

Thus, the net power delivered to the capacitor is:

$P - 2fqPt/C$

The energy on the capacitor as a function of time is then given by:

$$E(T) = \int_0^T (P - 2fqPt/c)\,dt$$

$$E(T) = P[T - qfT^2/C]$$

Since $E=\frac{1}{2}CV^2$, we have $$V = \sqrt{\frac{2P(T - qfT^2)/C}{C}}$$

$$V = \sqrt{\frac{2P(TC - qfT)}{C^2}}$$

$$V = \frac{\sqrt{2PT}}{C}\sqrt{C - qfT}.$$

This can be separated into 2 terms by squaring V:

$$V^2 = \frac{2PT}{C^2}[C - qfT]$$

giving:

$$V^2 = \frac{2PT}{C} - \frac{2PT^2qf}{C^2}$$

and, finally:

$$V = \left(\frac{2PT}{C} - \frac{2PT^2qf}{C^2}\right)^{\frac{1}{2}},$$

where the left-most term represents conventional capacitor charging without the extraction of the MVT nibble energy and the term right-most term represents that extraction.

Figure 9:
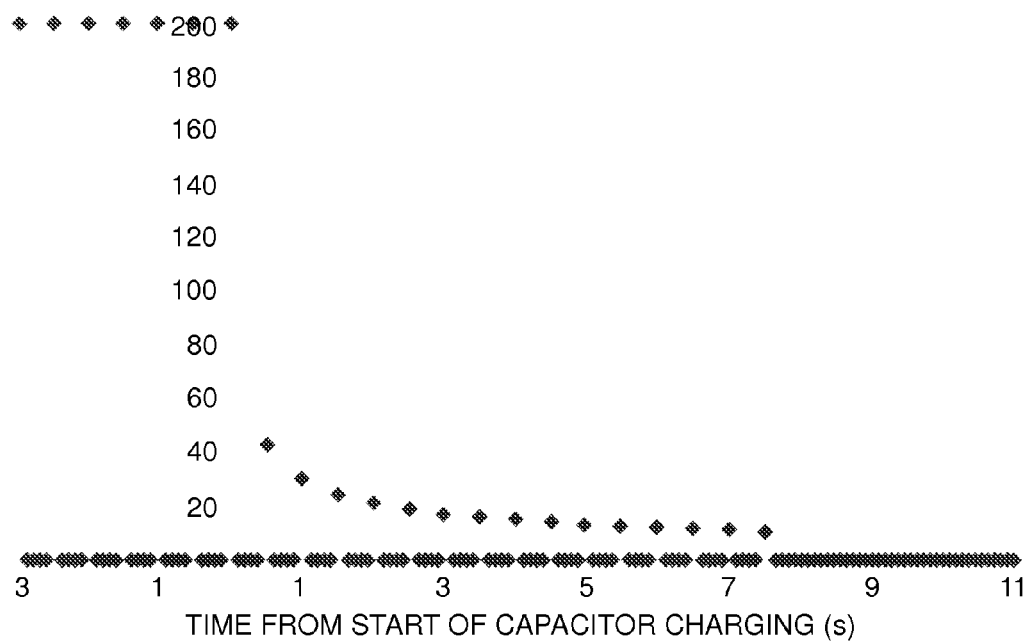
FIG. 9 is a chart depicting the MVT pulse duration as a function of time for an embodiment in which successive pulses are progressively narrowed as the capacitor voltage is increased during charging.

FIG. 9 is a chart depicting the MVT pulse duration for OSC pulses as a function of time for an embodiment in which successive pulses are progressively narrowed as the capacitor voltage is increased during charging. This is given by the following equations:

$I = I_r(1 + d_c/d)$ (from classical strength-duration theory).
A rheobase current ($I_r$) of about 1 ampere is sufficient to produce good cardiac output with external patches. Assuming a skeletal muscle stimulation chronaxie value of $d_c=150$ μs this gives a required current of:

$2A = I_r(1 + 150 \text{ μs}/150 \text{ μs})$ for a 150 μs pulse in this example.
In general (assuming the typical 1 A rheobase)

$I = (1 + d_c/d)$ $dI = d + d_c$ $d(I-1) = d_c = 150$ μs

Since I=V/R, we have:

$$d = \frac{150 \text{ μs}}{V/R - 1}$$

Since the metric of stimulation capability of a pulse is the charge, the pulse duration d is approximately inversely proportional to the voltage that is applied. Thus, as the capacitor voltage is increased during the charging time from 0 to 7.5 seconds in this example, the pulse duration is varied from about 45 μs down to about 10 μs. This gives a constant charge of approximately 300 microcoulombs. At the end of the 7.5 seconds, no pulses are delivered and the main shock capacitor is merely being topped off for the shock.

Figure 10:
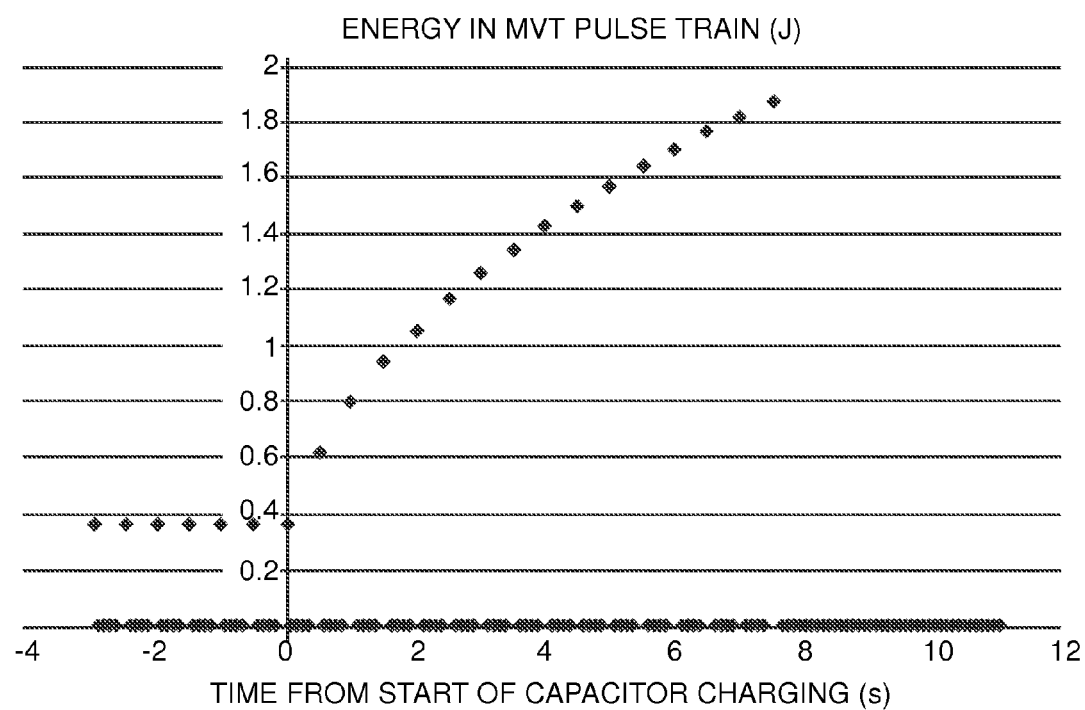
FIG. 10 is a chart illustrating the energy cost of delivering the stimulation charge by using narrow pulses of higher voltage according to one embodiment.

FIG. 10 is a chart illustrating the energy cost of delivering the stimulation charge by using narrow pulses of higher voltage according to one embodiment. Even though the charge applied to the patient with each pulse is kept constant by keeping the pulse duration d inversely proportional to the voltage, the energy is not constant.

$$d = \frac{150 \text{ μs}}{V/R - 1} \sim \frac{150 \text{ μs}}{V/R}$$

$\text{Energy} = dV^2/R = [150 \text{ μs} * R/V]V^2/R = 150 \text{ μs} * V$

The energy per pulse increases with the voltage and thus the energy in each pulse train increases from less than 0.4 joules up to almost 2.0 joules by the time the electrical CPR is terminated at 7.5 seconds in the example quantified here. This energy cost slightly interferes with the charging of the main capacitor and is what causes the small stair steps in FIGS. 6 and 8. However, it is not sufficient to halt the charging of the capacitor since, even at the maximum energy loss at 7.5 seconds, the medium voltage therapy is never more than 10% of the typical 22-watt charging ability of the exemplary charging circuitry for external devices (or 12 watts for a typical ICD).

In this example, the total cost in terms of charge time with the addition of MVT is less than one additional second. Moreover, this cost is far outweighed by the benefits of MVT.

Figure 11:
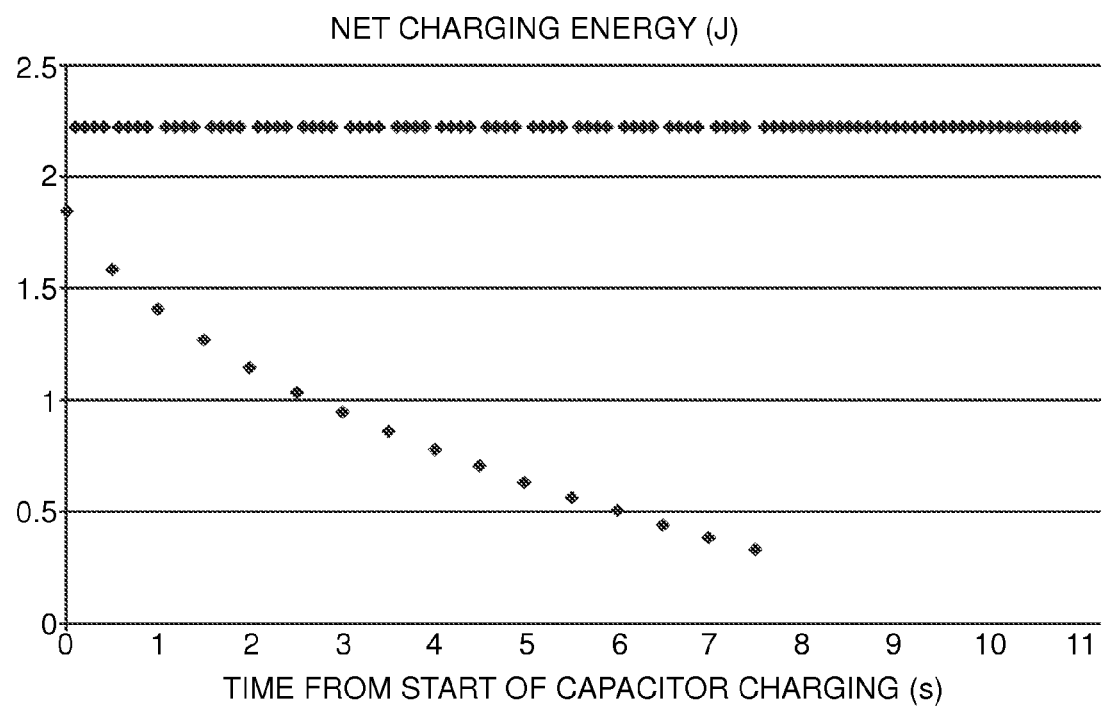
FIG. 11 is a chart illustrating the net charging energy per 0.1 second (100 ms) period according to one embodiment.

FIG. 11 is a chart illustrating the net charging energy per 0.1 second (100 ms) period according to one embodiment. Since the charging circuit in the exemplary external device embodiment is capable of delivering 22 watts, it delivers an energy of 2.2 joules per 100 ms time period. Even at the maximum MVT energy requirement of almost 2 joules per pulse train, at 7.5 seconds, there is still sufficient energy being delivered to the capacitor to charge it in full in this example.

In another approach to solving the problem of delivering MVT while charging the capacitor for defibrillation therapy, the delivery circuit includes a provision for stepping down the higher voltage stored in the capacitor to a voltage suitable for MVT. In this approach, a switching regulator such as a buck regulator is employed to produce a reduced voltage at the top of the H-bridge circuit. This approach essentially chops each individual MVT pulse into a plurality of even narrower pulses that have varying pulse widths. This pulse width modulated (PWM) power signal is then filtered so that its average value so that its spectral content applied to the patient is similar to that of conventional MVT pulses.

Figure 12:
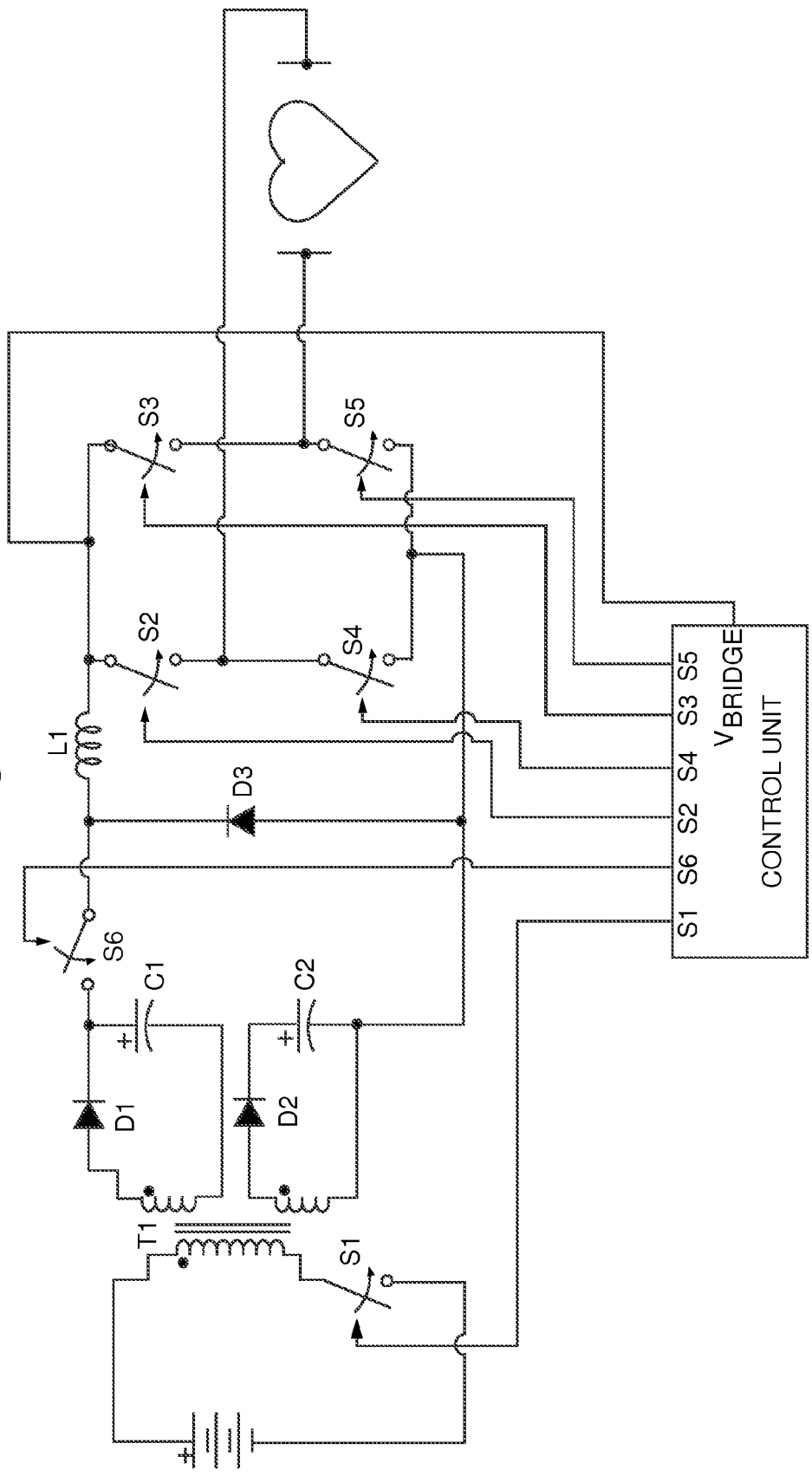
FIG. 12 is a simplified schematic diagram illustrating modifications that can be made to the circuit of FIG. 4 to accommodate a switching regulator according to one example embodiment.

FIG. 12 is a simplified schematic diagram illustrating modifications that can be made to the circuit of FIG. 4 to accommodate a switching regulator according to one example embodiment. In this embodiment, the added components include switch S6, inductor L1, and diode D3. The control unit controls switch S6 in a rapid switching mode that using pulse width modulation (PWM) based on voltage feedback signal $V_{bridge}$. Inductor L1 integrates the switched power signal to provide a substantially constant voltage at the top of the H-bridge. The value of inductor L1 is such that it is inconsequential to the MVT pulse attributes, though it will tend to slow the rise and fall times of the pulses by some small amount, which may even be a desired result in some cases. Diode D3 provides a current return path for the part of the switching cycle of switch S6 when the switch is open. This smoothing of the currents can provide an additional benefit for defibrillation therapy since the high initial peak current is somewhat damaging to the heart and does not provide help with defibrillation.)

In a related embodiment, the control unit is configured such that, at the conclusion of each MVT pulse (composed of a PWM signal), switch S6 is opened to stop the flow of current from the capacitors before the H-bridge switches are opened. In this regime, the H-bridge switches delivering the MVT current to the patient (e.g., S2-S5, or S3-S4) remain closed for a short time period that is sufficient to allow the energy magnetically stored in inductor L1 to dissipate. This prevents inductor L1 from developing a voltage spike due to the collapse of the magnetic field in L1 if the current through the inductor were suddenly interrupted. In a related embodiment, shoot-through is utilized to internally dissipate the energy stored in inductor L1 by shorting a single leg of the H-bridge (e.g., S2-S4) upon opening of switch S6.

Figure 13:
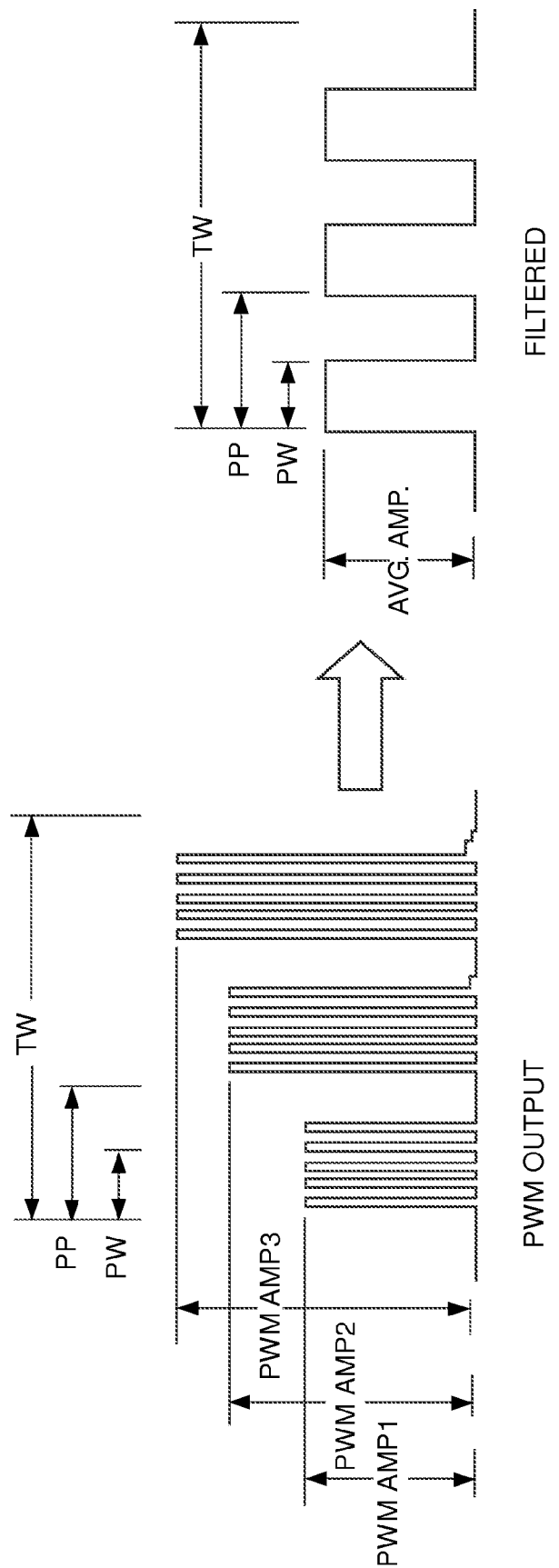
FIG. 13 is a diagram illustrating the general operation of the PWM circuitry of FIG. 12 for generating controlled-amplitude individual MVT pulses according to one embodiment.

FIG. 13 is a diagram illustrating the general operation of the PWM circuitry of FIG. 12 for generating controlled-amplitude individual MVT pulses according to one embodiment. The PWM output on the left-hand side of FIG. 13 represents the voltage at the cathode of D3. Note that the voltage waveform is not drawn to scale in this schematic diagram. As depicted, successive MVT pulses are generated as the capacitor voltage increases due to charging of the capacitor. These peak voltages are indicated as PWM Amp1, PWM Amp2, and PWM Amp 3. Switch S6 switches the capacitor in and out of the circuit to produce a switched voltage. The duty cycle of this switching produces an average voltage that is the same for successive individual MVT pulses. Thus, for an increasing capacitor voltage, the duty cycle is reduced. The inductor L1 filters the peaks and valleys of the switched waveform to produce a steady (non-switched) average voltage with none to negligible ripple. The filtering may be accomplished with a more elaborate filtering network using one or more additional filtering capacitors or inductors in other embodiments. The filtered waveform is depicted on the right-hand side. Each individual MVT pulse has the same pulse amplitude equal to Avg. Amp. The pulse width PW, pulse period PP, and train width TW are substantially unaffected.

In a related embodiment, the variable pulse width technique of transferring a common amount of charge to the patient with each pulse is used in conjunction with the PWM technique of adjusting the average pulse amplitude for each individual pulse to achieve greater control of the MVT pulse current and duration.

Figure 14A:
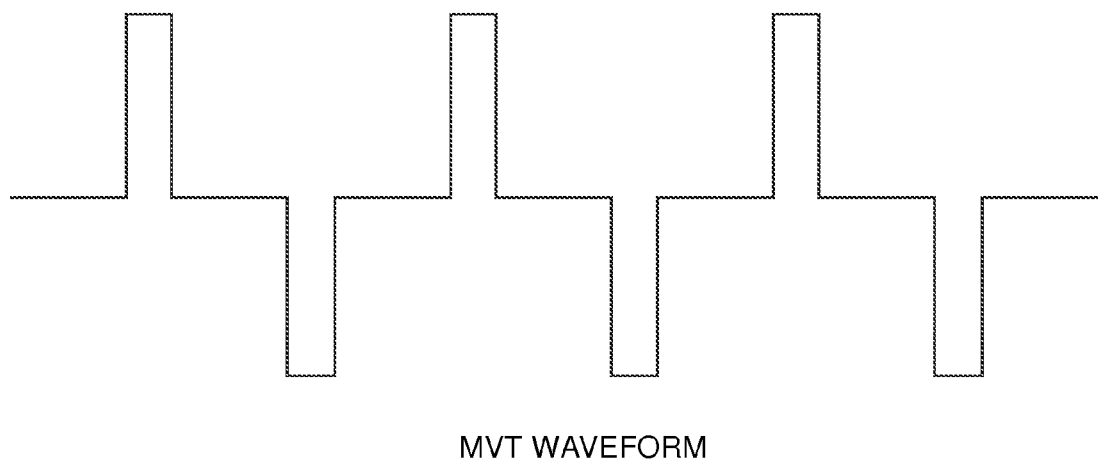
FIGS. 14A-14B are diagrams illustrating exemplary MVT waveforms according to another aspect of the invention.
Figure 14B:
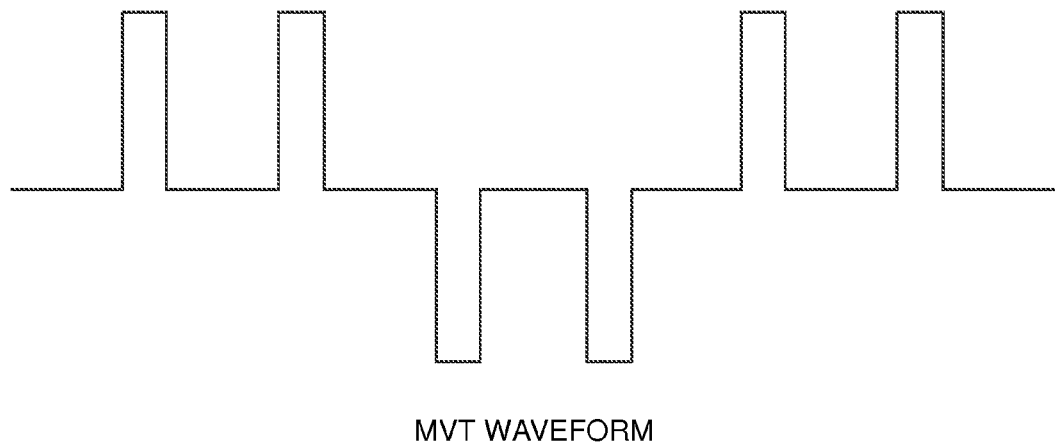

FIGS. 14A-14B are diagrams illustrating exemplary MVT waveforms according to another aspect of the invention. As depicted, the MVT waveform includes pulses in both polarities. The benefit of this technique is based on the recognition that muscle is stimulated far more efficiently with a negative or "cathodal" pulse. Thus, more muscle tissue near the negative electrode will be stimulated than the muscle tissue near the positive electrode. Thus, by alternating the polarity, embodiments of this invention capture more total muscle mass, and more widely distributed muscle mass. In addition, the captured muscle mass, as a whole, experiences less fatigue by virtue of having certain portions that are less frequently stimulated. These portions are muscle tissue that is captured when the MVT is applied in one polarity but not the other.

In the embodiment of FIG. 14A, each successive individual MVT pulse is of an alternating polarity. In the embodiment of FIG. 14B, the polarity changes for every two pulses. In other embodiments, the polarity can changed for every $n^{th}$ pulse, for example. In general, it is beneficial for the polarity of the MVT to be alternated relatively frequently, though in related embodiments, the polarity is alternated between successive pulse trains, or every $m^{th}$ pulse train. Also, it is generally preferable for the alternating polarity to be approximately evenly distributed between positive and negative pulses, though it does not have to be exactly evenly balanced.

The alternating polarity MVT pulses can be supplied using the H-bridge circuitry discussed above with reference to FIGS. 4 and 12 by alternating the current flow through switches S2-S5 and S3-S4.

Figure 15:
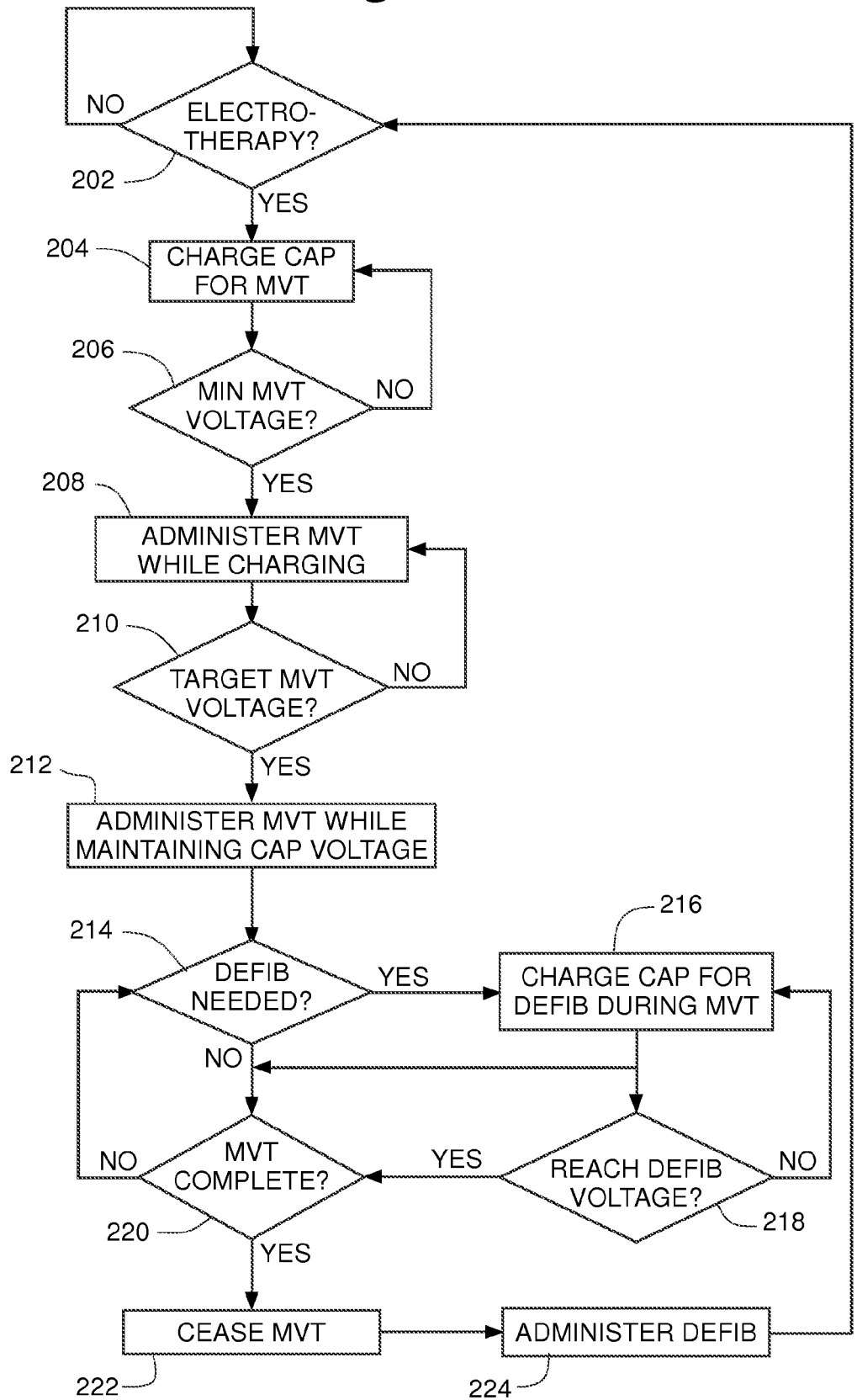
FIG. 15 is a flow diagram illustrating a basic operational algorithm for an electrotherapy device according to one embodiment.

FIG. 15 is a flow diagram illustrating a basic operational algorithm for an electrotherapy device according to one embodiment. In this electrotherapy device, the charging circuit and energy storage capacitor is shared for MVT and defibrillation therapies. At 202, the controller of the device checks the patient and determines a need for electrotherapy, MVT, defibrillation, or both. If electrotherapy is called for, at 204 the controller operates the charging circuit to begin charging the capacitor for MVT. At 206 a check is made if the minimum voltage for MVT is reached, at which point the MVT can be started at 208, while the capacitor continues charging. To apply MVT during charging, one or more techniques described above are employed to maintain an approximately constant charge transfer to the patient in each MVT pulse. At 210, a determination is made if the target MVT voltage is reached in the capacitor. This is a voltage at which the MVT can be applied most efficiently with the best effectiveness. In the examples provided above, this voltage is on the order of 150 volts for an external device, though other target voltages can certainly be used as appropriate. Until the target voltage is reached, the capacitor continues to be charge during MVT administration. Once reached, the target voltage can be maintained for some period of time to apply MVT at 212 for a prescribed time duration (or as needed based on continued patient monitoring).

At 214, a determination may be made as to whether defibrillation is needed. This is because the MVT might have converted the patient's arrhythmia although this is not the primary objective of the MVT. If defibrillation is called for, the capacitor is further charged up at 216 to the prescribed defibrillation voltage. At 218 a check is made to either continue charging or proceed. During this time, MVT can be continued according to one type of embodiment.

At 220, a check is made whether MVT should be concluded. This inquiry can occur during or after each check of the capacitor voltage during charging, as shown in FIG. 15. The need to conclude MVT may arise from the prescribed time for applying defibrillation being reached according to the device's rescue algorithm parameters. Otherwise, the MVT may be continued in some embodiments, even upon reaching of the defibrillation voltage. When it is time to apply the defibrillation, 222, MVT is ceased, and the defibrillation shock is applied at 224. The defibrillation shock is preferably applied very soon after cessation of the MVT, such as within 5 seconds, 3 seconds, 1, second, etc., depending on the capabilities of the discharge circuitry and on the rescue protocol of the electrotherapy device. The patient is then checked, and the process repeated if necessary.

The embodiments above are intended to be illustrative and not limiting. Additional embodiments are within the claims. In addition, although aspects of the present invention have been described with reference to particular embodiments, those skilled in the art will recognize that changes can be made in form and detail without departing from the spirit and scope of the invention, as defined by the claims.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

What is claimed is:

1. An improved multi-modal electrotherapy apparatus including circuitry for administering defibrillation therapy and for administering medium voltage therapy (MVT) as a distinct therapy from cardioversion and pacing therapies to force compression of the heart, the improvement comprising:
a combined-use bank of at least one capacitor for storing energy to be administered as defibrillation therapy and MVT;
a combined-use discharge circuitry electrically coupled between the combined-use bank of at least one capacitor and patient terminals for selectively administering energy from the bank of at least one capacitor according to a plurality of controllable waveforms as either defibrillation therapy or MVT;
a controller electrically coupled to the combined-use discharge circuitry and configured to cause the discharge circuitry to apply the MVT from the bank of at least one capacitor while the bank of at least one capacitor undergoes charging in preparation for administration of the defibrillation therapy.

2. The improved multi-modal electrotherapy apparatus of claim 1, wherein the controller is configured to cause the discharge circuitry to apply the MVT as packets of variable-width pulses, with each individual pulse having a pulse width approximately inversely proportional to a voltage to which the bank of at least one capacitor is charged.

3. The improved multi-modal electrotherapy apparatus of claim 1, wherein the controller is configured to cause the discharge circuitry to apply the MVT as packets of reduced-amplitude pulses that have their amplitude reduced in inverse proportion to an increase in voltage to which the bank of at least one capacitor is charged.

4. The improved multi-modal electrotherapy apparatus of claim 1, wherein the controller is configured to cause the discharge circuitry to apply the MVT as packets of pulses that provide a generally consistent charge transfer to the patient from one pulse to the next.

5. The improved multi-modal electrotherapy apparatus of claim 1, wherein the controller is configured to cause the discharge circuitry to apply the MVT as packets of pulses having variable pulse polarity such that different ones of the patient terminals variably provide a cathodal pulse to the patient as part of the administration of the MVT.

6. The improved multi-modal electrotherapy apparatus of claim 1, wherein the bank of at least one capacitor has a capacitance C and the voltage V on that capacitor is approximated as $$V = \left(\frac{2PT}{C} - \frac{2PT^2 qf}{C^2}\right)^{\frac{1}{2}},$$

wherein T represents the time (in seconds) from the start of charging of the capacitor, f represents a train rate of the MVT (in pulses per second), P represents a constant charging power, and q represents an amount of charge transferred to the patient per MVT pulse.

7. An improved multi-modal electrotherapy apparatus including circuitry for administering defibrillation therapy and for administering medium voltage therapy (MVT) as a distinct therapy from cardioversion and pacing therapies to force compression of the heart, the improvement comprising:
a combined-use bank of at least one capacitor for storing energy to be administered as defibrillation therapy and MVT;
a combined-use discharge circuitry electrically coupled between the combined-use bank of at least one capacitor and patient terminals for selectively administering energy from the bank of at least one capacitor according to a plurality of controllable waveforms as either defibrillation therapy or MVT;
a controller electrically coupled to the combined-use discharge circuitry and configured to cause the discharge circuitry to administer the defibrillation therapy within 5 seconds after administration of the MVT from the bank of at least one capacitor.

8. The improved multi-modal electrotherapy apparatus of claim 7, wherein the controller is configured to cause the discharge circuitry to administer the defibrillation therapy within 3 seconds after administration of the MVT from the bank of at least one capacitor.

9. The improved multi-modal electrotherapy apparatus of claim 7, wherein the controller is configured to cause the discharge circuitry to administer the defibrillation therapy within 1 second after administration of the MVT from the bank of at least one capacitor.

10. The improved multi-modal electrotherapy apparatus of claim 7, wherein the controller is configured to cause the discharge circuitry to apply the MVT as packets of variable-width pulses, with each individual pulse having a pulse width approximately inversely proportional to a voltage to which the bank of at least one capacitor is charged.

11. The improved multi-modal electrotherapy apparatus of claim 7, wherein the controller is configured to cause the discharge circuitry to apply the MVT as packets of reduced-amplitude pulses that have their amplitude reduced in inverse proportion to an increase in a voltage to which the bank of at least one capacitor is charged.

12. The improved multi-modal electrotherapy apparatus of claim 7, wherein the controller is configured to cause the discharge circuitry to apply the MVT as packets of pulses that provide a generally consistent charge transfer to the patient from one pulse to the next.

13. The improved multi-modal electrotherapy apparatus of claim 7, wherein the controller is configured to cause the discharge circuitry to apply the MVT as packets of pulses having variable pulse polarity such that different ones of the patient terminals variably provide a cathodal pulse to the patient as part of the administration of the MVT.

* * * * *